(12) United States Patent
Wang et al.

(10) Patent No.: US 7,842,006 B2
(45) Date of Patent: Nov. 30, 2010

(54) THROMBECTOMY MICROCATHETER (75) Inventors: Guiren Wang, Huntsville, AL (US);
Shivshankar Sundaram, Madison, AL (US); Kapil Pant, Huntsville, AL (US);
Jianjun Feng, Cincinnati, OH (US);
Peter Storm, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 0 days.

(21) Appl. No.: 11/561,303

(22) Filed: Nov. 17, 2006

(65) Prior Publication Data
US 2008/0119780 A1 May 22, 2008

(51) Int. Cl.
*A61B 17/22* (2006.01)
(52) U.S. Cl. ...................................................... 604/22
(58) Field of Classification Search ................... 604/22, 604/503; 606/7, 13
See application file for complete search history.

(56) References Cited

U.S. PATENT DOCUMENTS

| 4,576,177 | A | * | 3/1986 | Webster, Jr. | 600/439 |
| 4,922,902 | A | * | 5/1990 | Wuchinich et al. | 604/22 |
| 4,936,281 | A | * | 6/1990 | Stasz | 600/439 |
| 5,269,779 | A | * | 12/1993 | Sogawa et al. | 606/15 |
| 5,318,014 | A | * | 6/1994 | Carter | 606/128 |
| 5,362,309 | A | * | 11/1994 | Carter | 604/22 |
| 5,725,494 | A | * | 3/1998 | Brisken | 604/22 |
| 5,735,811 | A | * | 4/1998 | Brisken | 604/22 |
| 5,891,133 | A | * | 4/1999 | Murphy-Chutorian | 606/7 |
| 5,916,210 | A | * | 6/1999 | Winston | 606/7 |
| 6,024,718 | A | * | 2/2000 | Chen et al. | 604/22 |
| 6,139,543 | A | | 10/2000 | Esch et al. | |
| 6,235,024 | B1 | * | 5/2001 | Tu | 606/41 |
| 6,296,619 | B1 | * | 10/2001 | Brisken et al. | 604/22 |
| 6,379,325 | B1 | * | 4/2002 | Benett et al. | 604/22 |
| 6,398,792 | B1 | * | 6/2002 | O'Connor | 606/128 |
| 6,508,775 | B2 | * | 1/2003 | McKenzie et al. | 601/2 |
| 6,524,271 | B2 | * | 2/2003 | Brisken et al. | 604/22 |
| 6,547,779 | B2 | * | 4/2003 | Levine et al. | 606/7 |
| 6,558,366 | B1 | * | 5/2003 | Drasler et al. | 604/508 |
| 6,676,637 | B1 | * | 1/2004 | Bonnette et al. | 604/165.02 |
| 6,685,722 | B1 | * | 2/2004 | Rosenbluth et al. | 606/200 |
| 6,692,456 | B1 | * | 2/2004 | Eppstein et al. | 604/22 |
| 6,719,718 | B2 | * | 4/2004 | Bonnette et al. | 604/22 |
| 6,733,451 | B2 | * | 5/2004 | Rabiner et al. | 600/439 |
| 6,767,353 | B1 | * | 7/2004 | Shiber | 606/159 |
| 6,805,684 | B2 | * | 10/2004 | Bonnette et al. | 604/22 |
| 6,824,551 | B2 | * | 11/2004 | Trerotola | 606/159 |
| 6,875,193 | B1 | * | 4/2005 | Bonnette et al. | 604/22 |
| 2001/0041880 | A1 | * | 11/2001 | Brisken et al. | 604/503 |
| 2002/0003385 | A1 | * | 1/2002 | Jones | 310/334 |

(Continued)

*Primary Examiner*—Kevin C Sirmons
*Assistant Examiner*—Michael J Anderson
(74) *Attorney, Agent, or Firm*—Tomas Friend (57) ABSTRACT

The present invention is an ultrasonic thrombectomy catheter that produces physical forces (shear rates) strong enough to emulsify obstructions such as thrombi and emboli without causing damage to arterial walls. This is accomplished by properly arranging piezoelectric transducers within a catheter and a tubular catheter head separated by a gap to generate acoustic streaming that simultaneously emulsifies the obstruction and sweeps resulting debris into a catheter lumen for removal. The open gap may be formed by supporting struts that connect the catheter to the catheter head. The design of the catheter tip allows the fabrication of catheters capable of removing partial or complete blockages from arteries and other vessels having diameters as small as 2 mm.

16 Claims, 13 Drawing Sheets

U.S. PATENT DOCUMENTS

2002/0133111 A1* 9/2002 Shadduck .................... 604/19
2002/0151825 A1* 10/2002 Rubenchik et al. ............. 601/2
2004/0171981 A1* 9/2004 Rabiner et al. ................ 604/20
2005/0075620 A1* 4/2005 Iger ........................... 604/500
2005/0215942 A1* 9/2005 Abrahamson et al. ......... 604/22

* cited by examiner

THROMBECTOMY MICROCATHETER

STATEMENT REGARDING FEDERALLY SPONSORED RESEARCH OR DEVELOPMENT

The U.S. Government may have certain rights in this invention pursuant to SBIR Contract Number: NIH IR43NS050011-01 awarded by the National Institutes of Health.

CROSS-REFERENCE TO RELATED APPLICATIONS

Not Applicable

INCORPORATED-BY-REFERENCE OF MATERIAL SUBMITTED ON A COMPACT DISC

Not Applicable

BACKGROUND OF THE INVENTION

1. Field of the Invention

The present invention is an apparatus for removing a thrombus or other blockage from an artery or other vessel. More specifically, the apparatus comprises a microcatheter containing a micro piezo electric fiber that generates shear flows capable of disrupting and removing blood clots in small blood vessels that are difficult or impossible to reach with conventional thrombectomy catheters. The shear forces required for thrombus disruption are produced through a tube effect created by the positioning of one or more piezo transducers relative to the opening of a tube or catheter head.

2. Description of Related Art

Currently known techniques for emulsifying and removing obstructions from arteries include the use of high velocity saline jets, pulsed laser emissions, direct mechanical disruption, and acoustic vibration. Descriptions of these techniques may be found in U.S. Pat. Nos. 6,676,6317; 6,719,718; 6,805,684; 6,875,193; 6,558,366; 6,368,318; 6,685,722; 6,767,353; 6,824,551; and 6,379,325, which are incorporated by reference in their entirety.

The foregoing techniques suffer from one or more the following drawbacks including damage to the arterial walls, blocking of smaller, downstream arteries with clot fragments, and catheter diameters limited to use in large arteries. Laser devices and photo-acoustic devices in which light energy is converted into acoustic waves generate excessive heat and can perforate arterial walls. Saline jets can cause vessel dissection. Removing obstructions by suction can also damage arterial walls.

Ultrasound technology has been developed to open blocked or restricted arteries. The following examples of this technology are incorporated by reference in their entirety. U.S. Pat. No. 6,024,718 discloses an ultrasound catheter that uses a piezoelectric element to generate ultrasonic energy to emulsify a thrombus via sonophoresis. The piezoelectric element in this device is located at the tip of the catheter and is shaped to provide the desired ultrasonic field. U.S. Pat. No. 6,398,792 discloses an angioplasty catheter tipped with an ultrasonic transducer to cause dissolution of a thrombus and to crack and soften the surrounding plaque. The ultrasonic waves form the transducer are localized to a selected portion of the artery by inflating a balloon downstream of the transducer. US 2002/0003355 describes an apparatus comprising a catheter tipped with a substrate that has one or more piezoelectric elements attached to the substrate's outer surface. US 2002/0133111 describes a neuro-thrombectomy catheter that uses transducers distributed along the catheter length to move fluid and debris through the lumen. The movement of fluid generates suction at the tip of the catheter that pulls a thrombus into the catheter lumen, where it is emulsified. US 2002/0151825 describes an atherectomy catheter that uses ultrasonic waves generated by a piezoelectric transducer coupled to a conically-shaped tip to emulsify a plaque or thrombus. US 2004/0171981 discloses a device for removing an occlusion from an artery using an elongated, flexible ultrasonic probe at the distal end of a catheter in conjunction with a thrombolytic drug. Transverse ultrasonic vibrations generate a "cavitational energy" that extends radially outward from the longitudinal axis of the probe to ablate the occlusion.

None of the devices described above use a piezo transducer positioned relative to a tube specifically to generate a tube effect resulting in acoustic streaming.

U.S. Pat. No. 6,139,543 and U.S. Pat. No. 6,547,779 disclose a flow apparatus for the disruption of clots and other occlusions in blood vessels. This device uses pulsed laser light to generate small, transient bubbles that alternately expand and collapse to pump fluid near the tip of a capillary, or small diameter catheter. Proper arrangement of optical fibers relative to the open end and side windows of the catheter tip generates a fluid flow in which fluid is ejected from the open end of the catheter tip and suctioned back into the catheter tip through the side windows. The '543 and '779 patents, incorporated by reference in their entirety, disclose that the flow apparatus can be used to remove obstructions by pushing the catheter tip through an obstruction and emulsifying it as it is suctioned into the side windows of the catheter. Alternatively, the fluid ejected from the tip of the catheter can be used to ablate an obstruction by placing the open end of the catheter against the surface of the obstruction. This device provides a means for disrupting obstructions in small arteries and is capable of generating fluid forces capable of disrupting clots.

The use of laser light to generate fluid streaming, as described in '543 and '779 patents, is distinct from the acoustic streaming produced by, the present invention. Laser-induced fluid streaming involves the localized heating and boiling of liquid to form bubbles that rapidly collapse. Pulsing the laser causes the repeated rapid formation and collapse of gas bubbles in liquid and generates excess heat in the process.

The present invention uses piezoelectric transducers to generate acoustic streaming of fluid capable of disrupting clots and other obstructions in arteries and other vessels without generating excessive heat or bubbles. Acoustic streaming has thus far been incapable of generating shear forces strong enough to disrupt clots in small vessels. The present invention overcomes the previous limitations of acoustic streaming in small vessels using combinations of vibrational modes and catheter head configurations that use an unexpected tube effect to generate enhanced acoustic streaming.

BRIEF SUMMARY OF THE INVENTION

The present invention is an ultrasonic thrombectomy catheter that produces physical forces (shear rates) strong enough to emulsify obstructions such as thrombi and emboli without causing damage to arterial walls. This is accomplished by properly arranging piezoelectric transducers within a catheter head having a distal opening and an open gap proximal to the distal end of the catheter head to generate acoustic streaming that simultaneously emulsifies the obstruction and sweeps resulting debris into a catheter lumen for removal. The open gap may be formed by supporting struts that connect a catheter head to a catheter or by tip windows located at the base (proximal end) of the catheter head. The design of the catheter tip allows the fabrication of catheters capable of removing partial or complete blockages from arteries and other vessels having diameters as small as 2 mm.

The present thrombectomy catheter uses one or more microfabricated piezo fibers within the head of a microcatheter. The head of the microcather comprises a distal opening and a gap or side windows. Obstructions are fragmented efficiently by strong fluidic motion that is generated by applying a voltage across the piezo fiber(s). The flow magnitudes necessary for disintegrating the obstruction are achieved by positioning the actuating fiber within the head of the microcatheter relative to the distal opening and gap or windows. In one embodiments the catheter has two lumens with the first serving to activate the thrombectomy device and the second to remove fragments of the obstruction. The fluid stream generated by the catheter head flushes obstruction fragments from the circulation into the second lumen to minimize the risk of re-occlusion downstream the obstruction in the vasculature. The second lumen can additionally or alternatively serve as a drug delivery port for an anti-thrombotic agent such as tissue plasminogen activator (tPA). Although designed for removing obstructions causing stroke, the microcatheter system can also be used in other arteries and vessels such as coronary, pulmonary, renal, hepatic, and peripheral arteries and veins as well as other natural or artificial vessels and ducts. Some of these applications may not require an embodiment of the invention having a second lumen for debris removal.

BRIEF DESCRIPTION OF THE SEVERAL VIEWS OF THE DRAWINGS

FIGS. 7A and B show cross sectional views of a double lumen embodiment of the invention.

FIGS. 8A and B show cross sectional views of an embodiment of the invention having multiple piezo transducers.

DETAILED DESCRIPTION OF THE INVENTION

Figure 1:
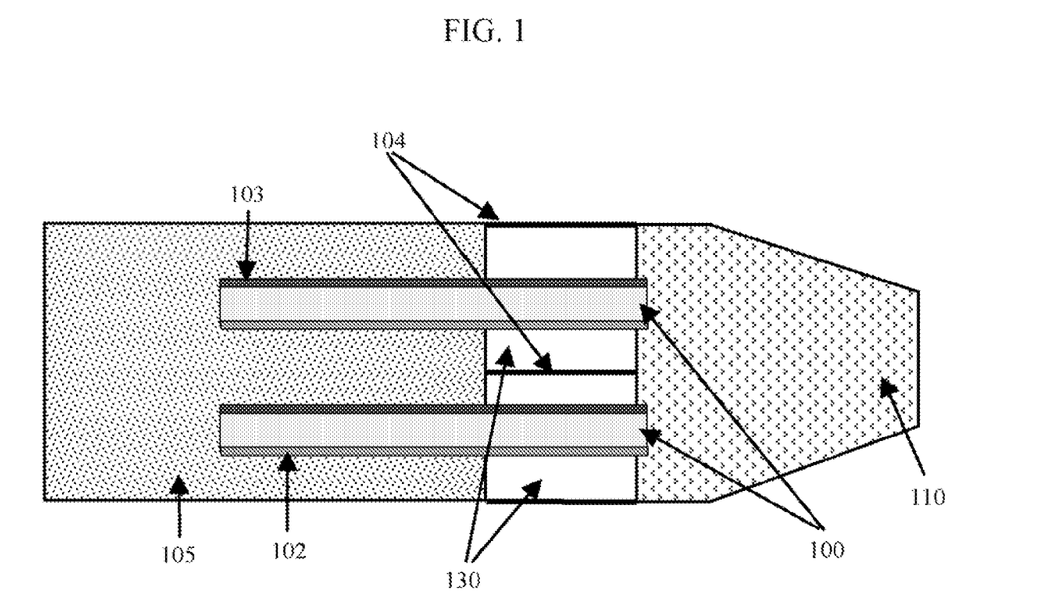
FIG. 1 shows a diagram of a first embodiment of the present invention.

FIG. 1 illustrates a longitudinal cross section of a first embodiment of the invention. Catheter 105 is connected to catheter head 110 by connecting struts 104. Catheter head 110 is a tube open at both ends (right). Catheter 105 and catheter head 110 are separated by a gap 130. Two piezo-electric transducers 100, each having opposing electrically conducting surfaces 102 and 103 for connection to electrical leads, not shown, are positioned such that the base of each transducer in located in the lumen of catheter 105 and the tip of each transducer is located just inside the lumen of catheter head 110. The position of each transducer tip relative to gap 130 is important for producing optimal acoustic streaming as shown in FIG. 2.

Figure 2:
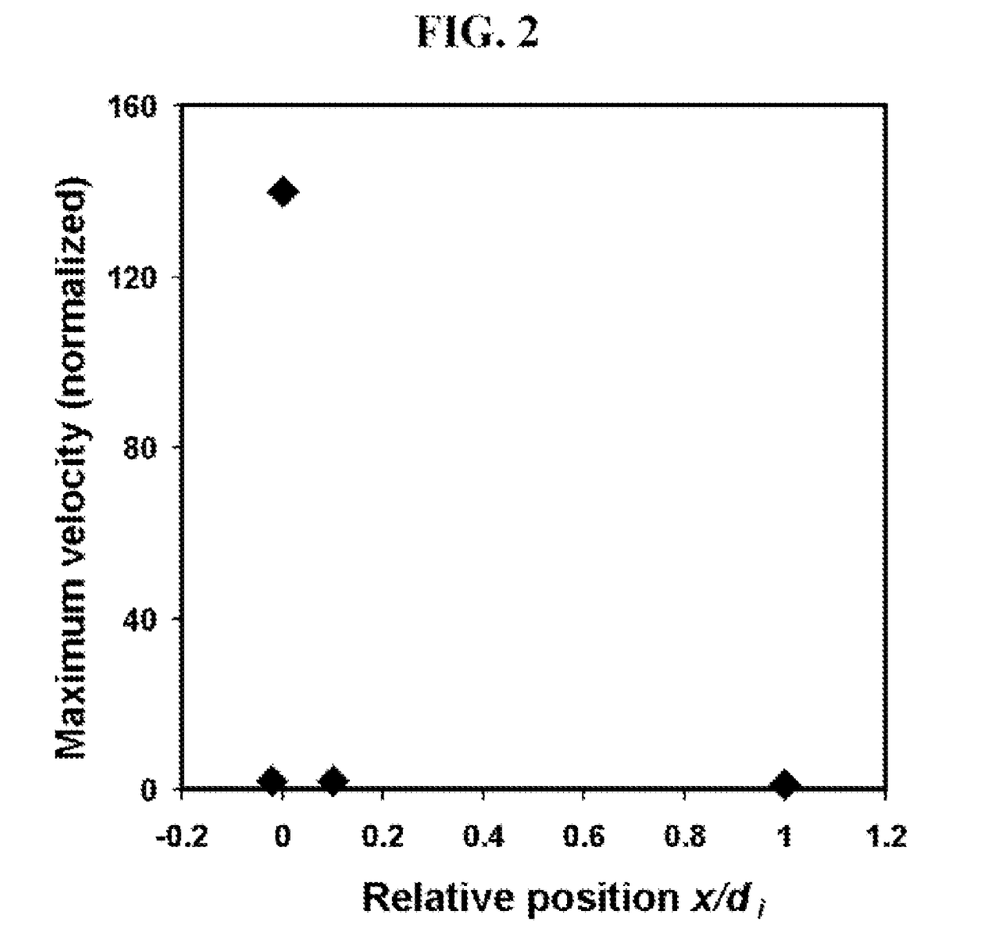
FIG. 2 shows experimental results demonstrating the tube effect.

FIG. 2 shows the results of flow visualization experiments for several different distances between the tip of a piezo transducer fiber and the proximal end of a catheter head. Configurations with the fiber located both inside and outside the tube were tested. The catheter head does not significantly influence the fluid motion until it is moved very close to the fiber tip. At this point, the flow field increases dramatically to a maximum velocity in excess of 140 mm/s. The synergetic effect between the fiber and tube to increase flow velocity helps produce the shear forces needed to disrupt vessel blockages. The optimal location of piezo tip relative to the catheter head, or tube, as well as the length of the gap between the catheter and catheter head depend upon the a number of factors including the diameter of the catheter head, the size and number of piezo transducers, and the frequency of vibration.

Figure 3:
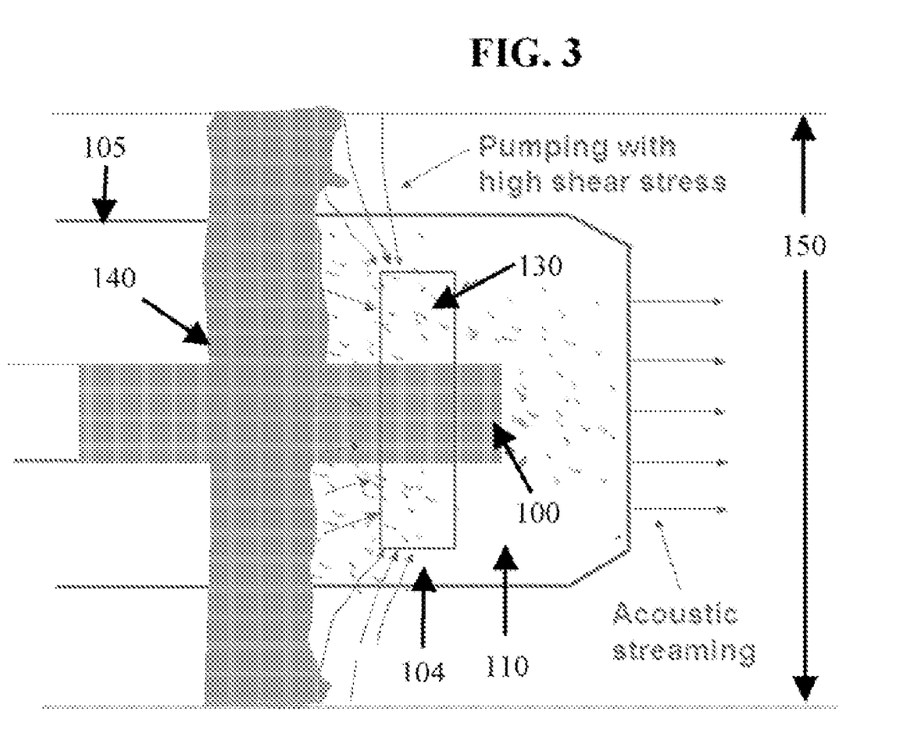
FIG. 3 is a schematic of a second embodiment of the present invention.

A second embodiment of the thrombectomy microcatheter, shown in FIG. 3, comprises a piezo transducer 100 that spans a gap 130 separating a catheter 105 and a catheter head 110 connected by struts, or structural members 104. A power supply and instrument control unit provide electrical power to the piezo transducer through leads that run the length of the catheter. The piezo transducer is insulated using an electrically insulating coating material. FIG. 3 shows one mode of operation for this embodiment in which the catheter head is pushed through a blood clot 140 within a blood vessel 150 and shear stresses produced by fluid flowing into the gap fragments the clot. Small arrows in the figure indicate the flow of liquid generated by acoustic streaming, including areas of high shear near the gap 130. Fragments of the clot may then be removed by suction through a liquid-filled catheter lumen (not shown).

Figure 4:
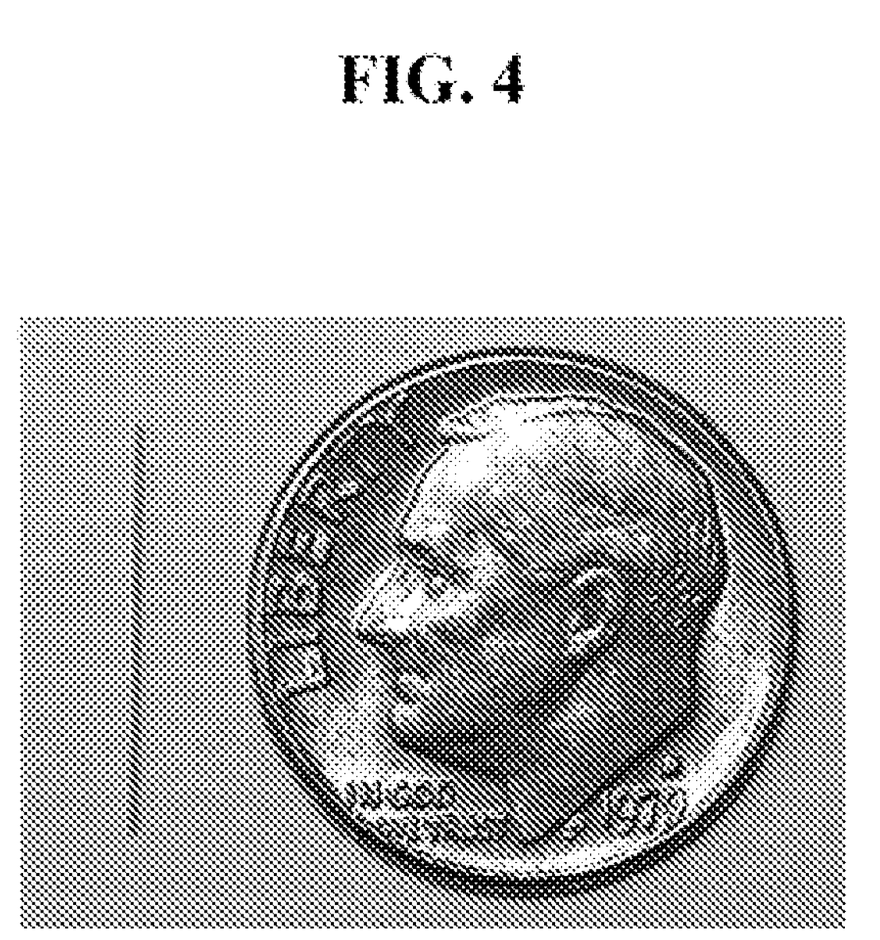
FIG. 4. illustrates the size of a Microscale SMC piezo transducer fiber.

The thrombectomy microcatheter comprises one or more piezo-fibers. FIG. 4 shows the size of one exemplary piezo ceramic fiber relative to a dime. The transducer has a cross section of 160 µm×340 µm. Other exemplary dimensions for a single fiber piezo transducer are around 1 mm×170 µm×60 µm and around 1 mm×120 µm×80 µm. The actual dimensions used for any embodiment of the invention depend for example, on the desired size of the head and the material comprising obstruction to be removed.

Figure 5:
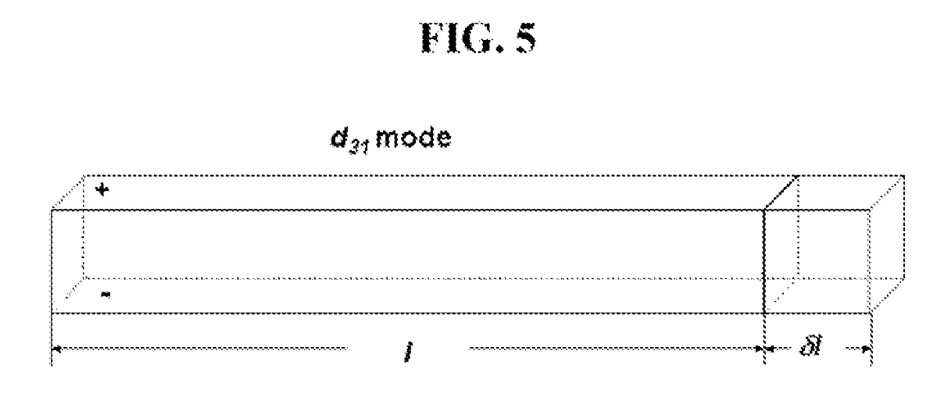
FIG. 5. shows the $d_{31}$ mode of vibration for a piezoelectric transducer of the invention.

The piezoelectric transducers of the present invention are different from those previously used in the art. The present invention comprises piezoelectric transducer fibers having cross-sectional dimensions that are small enough to be used to disrupt clots in vessels as small as 2 mm in diameter. Unlike the piezoelectric transducers previously described for disrupting clots, the present piezoelectric transducers operate in a $d_{31}$ vibrational mode that is aligned with the length of the piezoelectric fiber and orthogonal to the applied electric field. Other piezo transducer-based thrombectomy devices use the $d_{33}$ vibrational mode. The $d_{31}$ vibrational mode normally produces less displacement of the piezo transducer and therefore less efficient acoustic streaming, than produced by the $d_{33}$ mode. The present invention overcomes the disadvantages related to the use of the $d_{31}$ vibrational mode to generate acoustic streaming capable of disrupting obstructions in blood vessels. FIG. 5 illustrates the $d_{31}$ vibrational mode induced in the piezo fiber to achieve acoustic streaming in the present invention. The length l changes during vibration by the distance δl. The electric field applied to generate vibration is shown by + and − and is orthogonal to the direction of vibration. High electric fields can be generated even at low applied voltages because the electrodes are separated by a very small distance.

Figure 6:
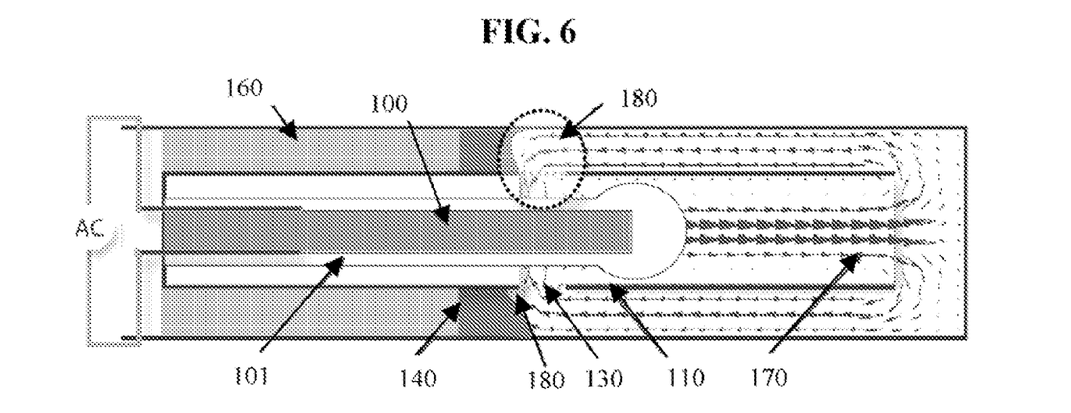
FIG. 6 illustrates one mode of use for the thrombectomy microcatheter.

FIG. 6 illustrates a longitudinal cross sectional view of the use of an embodiment of the thrombectomy microcatheter. One or more structural members (not shown) connect the catheter 105 and catheter head 110. The proximal end of a piezoelectric transducer 100 is located within the catheter 105 and the distal end is located inside catheter head 110. A layer of insulating material 101 coats the transducer, preventing contact between the piezo element and blood. The piezo 100 is driven by an AC field, which induces longitudinal vibration of the transducer. The vibrating transducer induces acoustic streaming 170 in the vessel lumen 160, which can be enhanced by the geometries of the gap 130 and connecting members. Acoustic streaming generates a region of high shear force 180 at the surface of the clot 140.

Figure 7:
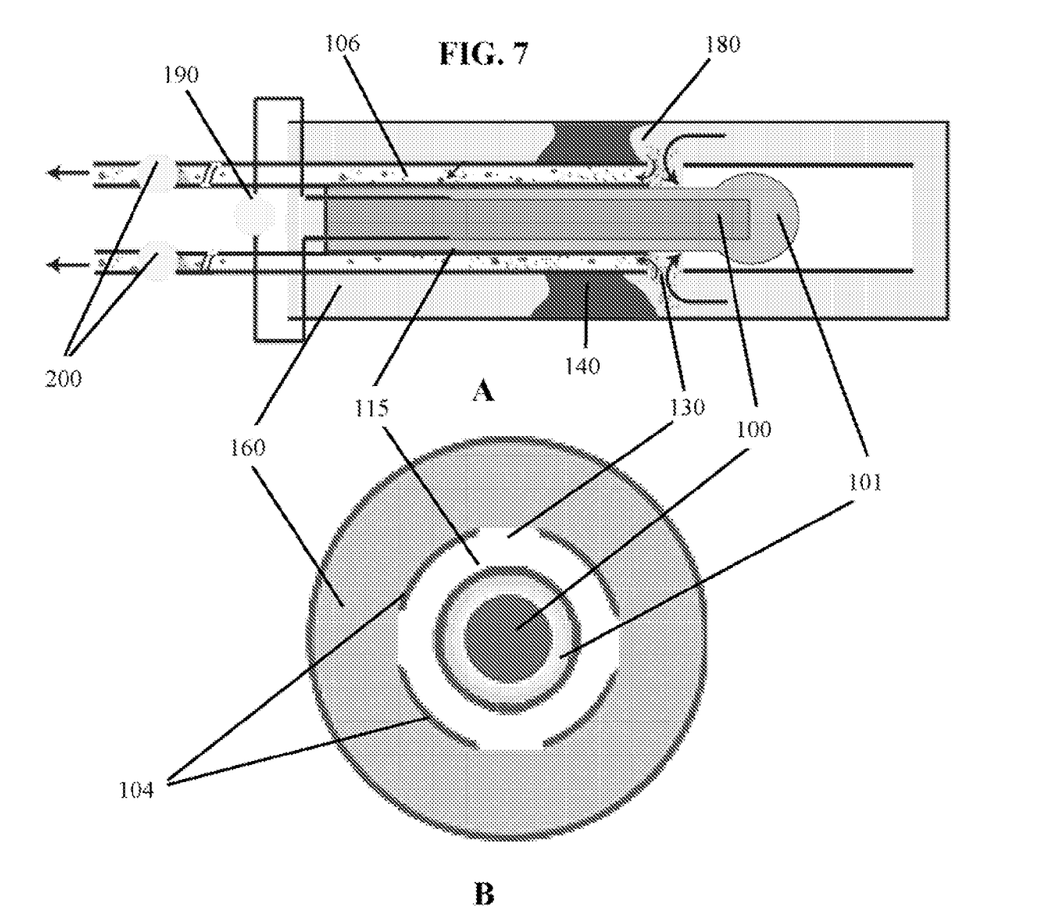

FIG. 7A is a longitudinal cross section view of an embodiment of the thrombectomy catheter comprising one piezo transducer 100 and four structural members 104 connecting catheter 105 and catheter head 110. The first lumen 106 houses the transducer 100 and transducer leads from the power supply 190, while the second lumen 115 is used to carry debris from the obstruction 140 out of the artery, into the catheter and out of the patient's body. In this embodiment, a fraction of the flow through the cgap 130 is diverted from areas of high shear 180 and is aspirated by suction out of the body by pump 200. The overall flow is balanced so as not to alter the acoustic streaming flow patterns in the blood vessel. FIG. 7B provides an end cross sectional view of the catheter head in the plane of gap 130.

Figure 8:
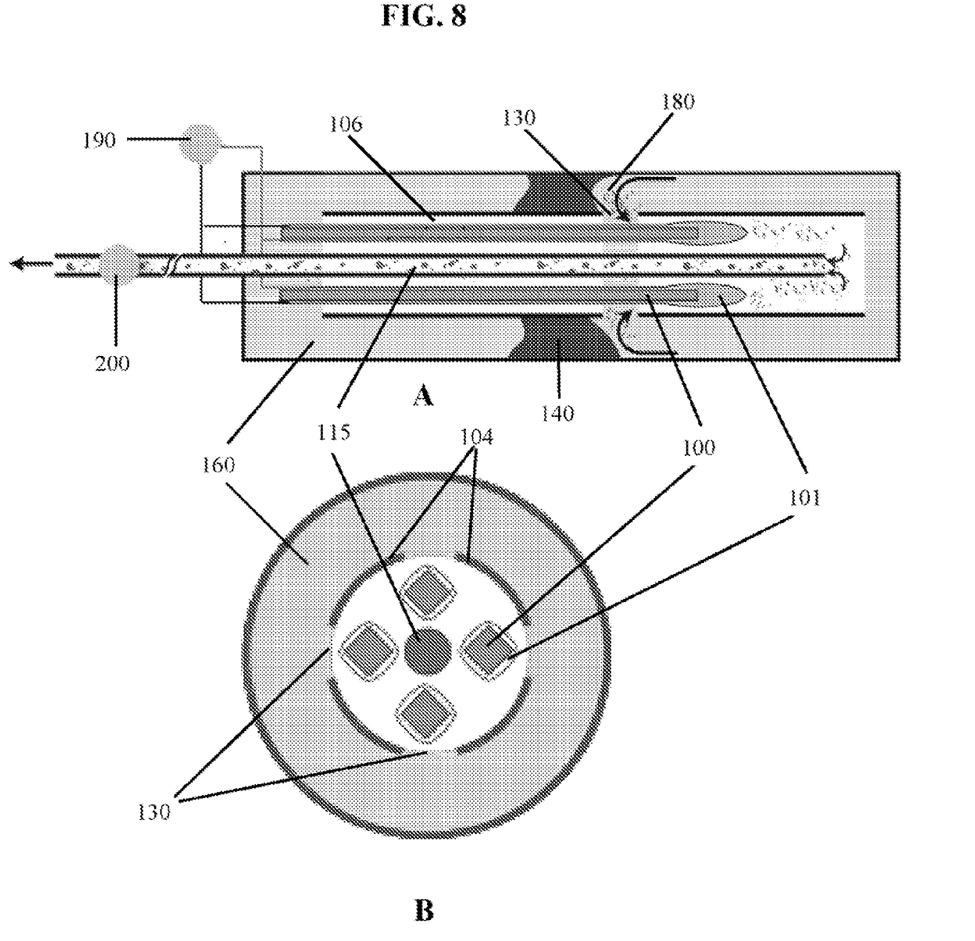

FIG. 8A shows a longitudinal cross section view of an embodiment of the present invention comprising four piezo transducers 100. A first lumen 106 serves as the active thrombectomy unit housing the inducers and leads from the power supply 190. A second lumen 115 serves to aspirate debris from areas of high shear 180 for removal by pump 200. FIG. 8B provides an end cross sectional view of the catheter in the plane of gap 130.

A number of piezoelectric thrombectomy catheter designs were analyzed using physics-based simulations. A prototype of the micro-scale active piezoelectric fiber (transducer) was fabricated and acoustic streaming caused by the piezo-actuated microcatheter was demonstrated and quantified. In-vitro experiments using clot stimulants were conducted to demonstrate clot disruption capability. The prototype thrombectomy catheter generated strong fluid flow patterns and successful break-up of clot an analogs in in-vitro experiments.

Figure 9:
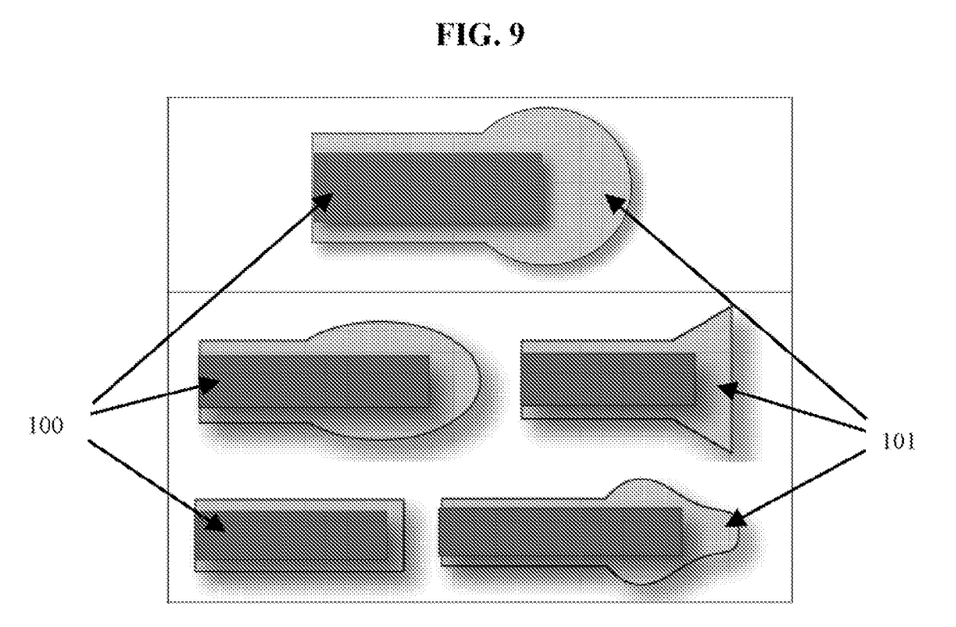
FIG. 9 shows exemplary shapes for material insulating a piezo transducer.

The performance of the catheter is influenced by several parameters including the size, number and location(s) of the actuator(s), the length location, and geometry of the gap with respect to the actuator(s), and the thickness and shape of the insulating material on the piezo transducer. For example the shape of the tip may be modified to alter the flow induced by the piezo transducer. FIG. 9 shows some exemplary shapes for insulating material 101 on the transducer 100. The manner in which the above parameters influence the operation of the thrombectomy microcatheter is described in the following experimental and computationally calculated examples.

Example 1

Piezo Fiber Testing

In-vitro experiments were conducted using a single piezo fiber transducer. The experiments were carried out by placing the piezo fiber in a rectangular flow chamber. Fluorescent microparticles suspended in deionized (DI) water, were used as tracers for flow visualization. A signal generator was used to drive the piezo transducer and an AC signal was modulated with a commercial voltage amplifier. An inverted epi-fluorescence microscope was used to visualize the flow inside the chamber generated by the piezo transducer. A high performance high speed digital CCD camera was used to record the flow. Since the camera exposure time is known, the recorded path lines of the microparticles were measured to estimate flow velocity. Experimental results demonstrated that the piezo transducer generates acoustic streaming, and the corresponding flow rate can been increased by manipulating the transducer relative to a small tube. The forcing frequency and voltage for the experiment was 50 kHz and 212 $V_{nms}$.

Example 2

Effect of Applied Frequency

Figure 10:
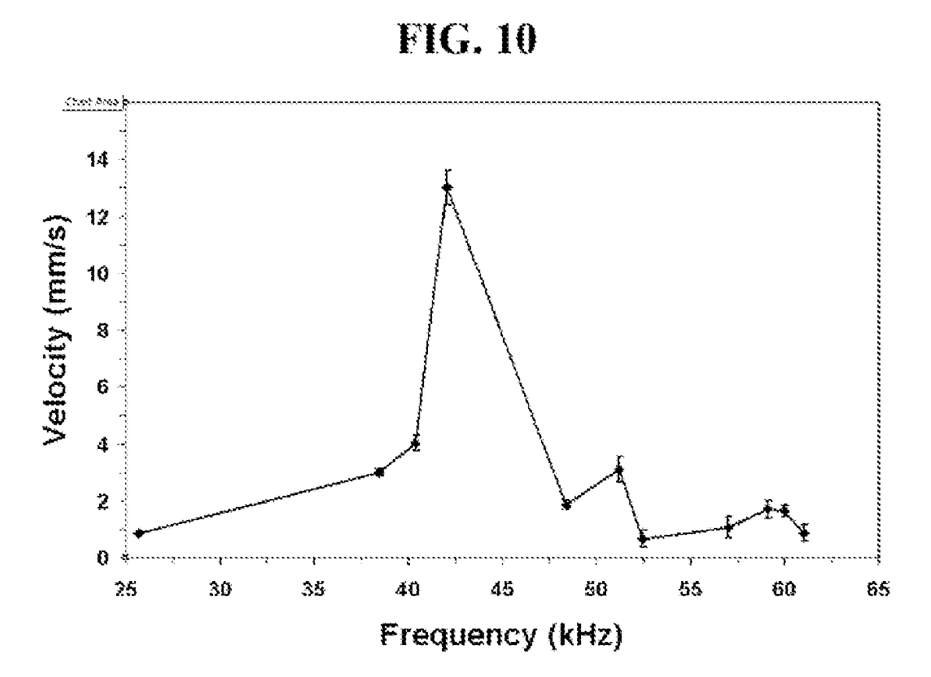
FIG. 10. is a graph showing acoustic streaming flow velocity versus frequency.

Experiments were conducted to obtain the resonance frequency for piezo transducers in order to maximize displacement and acoustic streaming. FIG. 10 to shows the effect of actuation frequency on the maximum acoustic streaming velocity near the tip of the fiber. The disturbance imparted by the piezo transducer to the fluid increases with frequency. For an applied frequency of 38 kHz, the streamlines are short and the maximum streaming velocity is approximately 3.0 mm/s near the piezo transducer tip. When the frequency is increased to 42 kHz, the streamlines are much longer and the maximum velocity increases sharply to 13 mm/s. With a further increase in frequency, the maximum velocity decreases to about 3.1 mm/s. This indicates that there is an optimal frequency, under which the strongest acoustic streaming is obtained.

Figure 11:
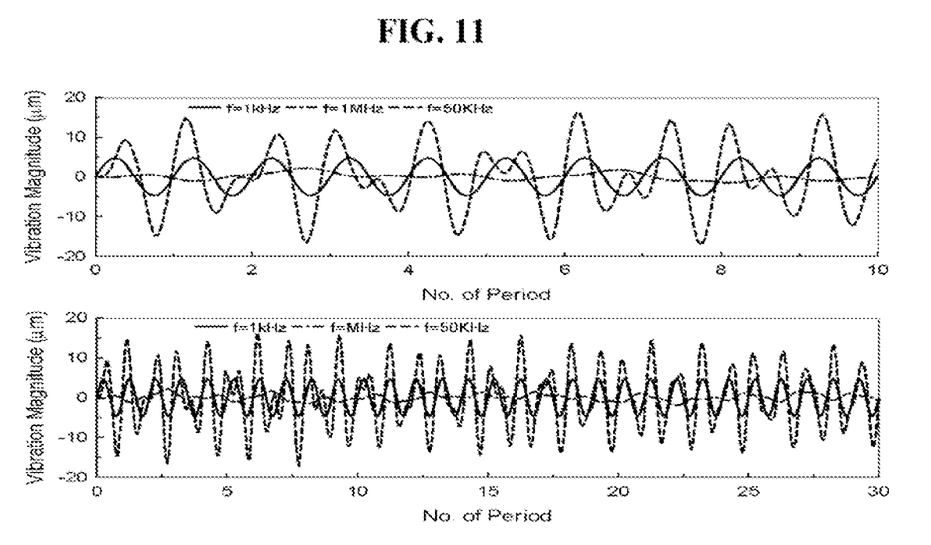
FIG. 11. shows the results of computational modeling of the effects of frequency on the magnitude of transducer vibration.

Computational analysis was undertaken to gain insights into the dependence of acoustic streaming on applied frequency. FIG. 11 shows the response (displacement) of the piezo tip upon application of electric fields of different frequency (10 kHz, 50 kHz and 1 MHz). At low frequencies, the piezo vibration is in phase with the applied signal. At higher frequencies, the motion of the transducer exhibits a complex bi- or tri-modal vibrational spectrum. The vibration amplitude increases approximately four times when the applied frequency is changed from 10 kHz to 50 kHz, but decreases sharply at 1 MHz.

Example 2

Effect of Applied Voltage

Figure 12:
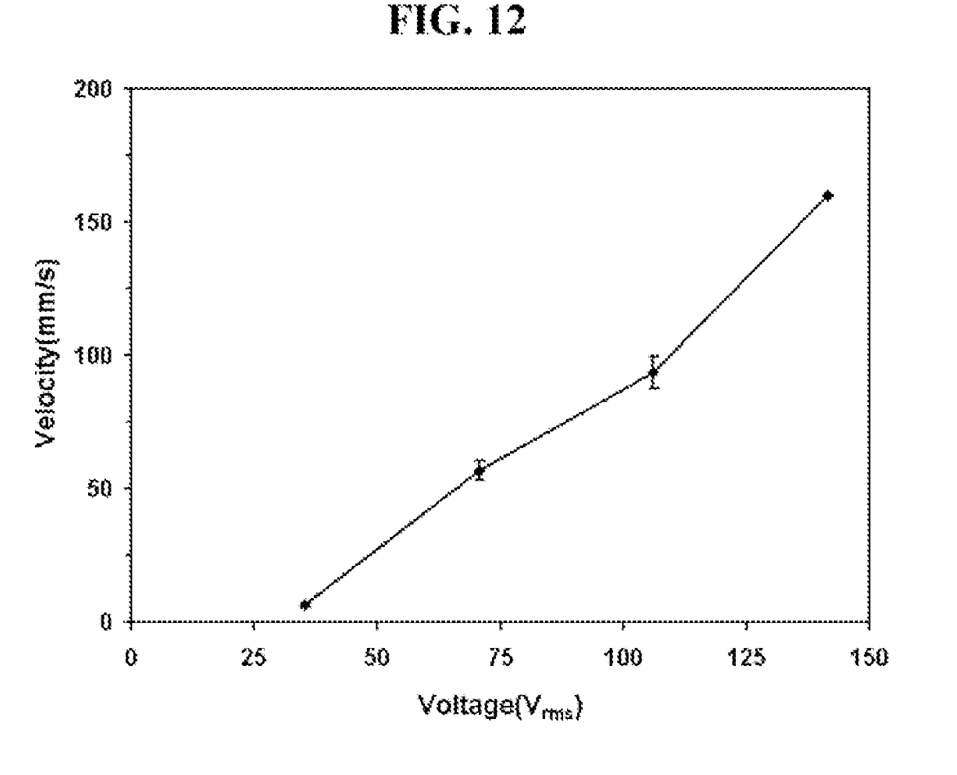
FIG. 12. is a graph illustrating the effects of applied voltage on acoustic streaming.

FIG. 12 shows the acoustic streaming in response to different applied voltages at the resonance frequency (42 kHz) obtained from the frequency characterization experiments. The maximal velocity scales with the applied voltage. The maximum streaming observed for a particular transducer depends on the piezo fiber size, its quality, and the insulation coating.

Example 3

Piezo Fiber Coatings

Thinner coatings are more effective in transmitting the vibrational energy from the transducer to the surrounding fluid. Coating thickness optimally ranges from 10 µm to 50 µm and should be uniform along the length of the transducer. The stiffness of the insulation material also affects the oscillation of the transducer with lower stiffness being preferred.

Figure 13:
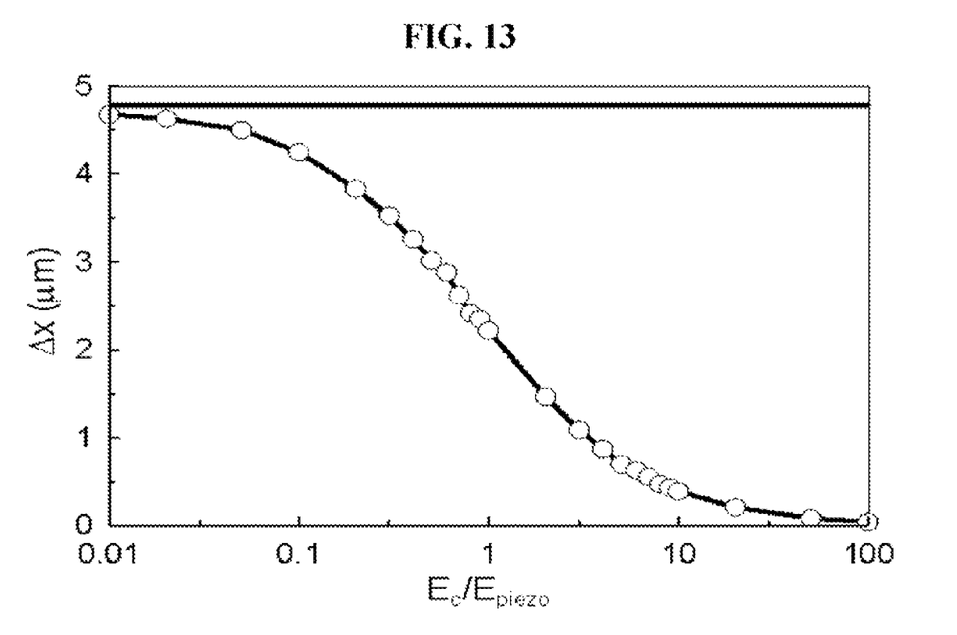
FIG. 13. is a graph showing the effects of coatings on actuator vibrational amplitude.

Computational simulations were carried out to identify optimal choices for coating material. FIG. 13 shows the effects of coating, material stiffness on the vibrational amplitude of a transducer. As the coating layer becomes stiffer the vibration magnitude is seen to decrease non-linearly for a given frequency. The dampening of piezo motion is significant for $E_c/E_{piezo} > 0.5$, with E being the Young modulus of elasticity and the subscripts c and piezo denote the coating and the transducer material properties. Therefore, coating materials softer than the piezo material preferred as insulation materials. Possible insulating materials include chemicals such acrylic conformal coating from Miller-Stephenson Products (Sylmar, Calif.), epoxy EP30LV® from Master Bond (Hackensack, N.J.), silicone, and polyurethane.

Example 4

Clot Disintegration Experiments

To demonstrate the capability of the piezo transducer for breakup the blood coats preliminary experiments were carried out using two different clot stimulants. The stimulants were inserted into or formed within 3 mm inner diameter tubes. A thrombectomy catheter prototype having a single piezo transducer was inserted thorough the clot stimulants and the piezo transducer was actuated using an applied voltage of 106 $V_{rms}$ and frequency of 98 kHz. Videotaped experimental observations were used to document processes in which the clot stimulants were disrupted arid aspirated from the tube. At the end of the experiments, only small parts of the clot stimulants remained in the tube.

A number of different specific embodiments of the invention have been referenced to describe various aspects of the present invention. It is not intended that such references be constructed as limitations upon the scope of this invention except as set forth in the following claims.

What is claimed is:

1. An apparatus for removing an obstruction from a physiological vessel in a subject, said apparatus comprising:
   a) a catheter comprising:
      i) a proximal end configured to connect to an electrical power supply,
      ii) a distal end connected to a proximal end of an open, tubular catheter head having a proximal end and a distal end and configured to be placed within the lumen of a physiological vessel,
      iii) a first lumen having a proximal opening configured to remain outside of the subject and a distal opening in the distal end of the catheter and facing the proximal end of the open tubular catheter head,
      iv) a gap separating the distal end of the catheter and the proximal end of the catheter head, said gap being configured to allow fluid in the physiological vessel to enter the proximal end of the open tubular catheter head and the distal opening of the first lumen,
      v) at least one structural member connecting the distal end of the catheter to the proximal end of the open tubular catheter head, and
      vi) at least one electrically insulated, elongated piezoelectric transducer that spans the gap between the distal end of the catheter and the proximal end of the open tubular catheter head such that a proximal end of the transducer is located inside the distal end of the catheter and a distal end of the transducer is located outside the catheter and either in the said gap or in the catheter head.

2. The apparatus of claim 1 wherein the catheter and catheter head are circular in cross section and the catheter and the catheter head are connected by two or more structural members.

3. The apparatus of claim 1 comprising a plurality of elongated peizo transducers that span the gap between the distal end of the catheter and the proximal end of the open tubular catheter head such that a proximal end of each transducer is located inside the distal end of the catheter and a distal end of each transducer is located outside the catheter and either in said gap or in the open tubular catheter head.

4. The apparatus of claim 1 wherein the distal end of the piezo transducer is located within 20 mm of the proximal end the catheter head.

5. The apparatus of claim 4 wherein the distal end of the piezo transducer is located within 1.0 mm of the proximal end the catheter head.

6. The apparatus of claim 1 and further comprising a second lumen, containing electrical leads configured to activate the at least one elongated piezo transducer.

7. The apparatus of claim 6 wherein the proximal opening of the first lumen is in fluid communication with a pump for removing fluid from the gap.

8. The apparatus of claim 3, wherein the plurality of piezo transducers are arranged around the distal opening of a first lumen located in the center of the distal end of the catheter.

9. The apparatus of claim 1 wherein the at least one structural member connecting the catheter to the catheter head comprises an extension of the catheter head connected to the catheter.

10. The apparatus of claim 1 wherein the piezo transducer oscillates in a $d_{3,1}$ mode.

11. A method for removing an obstruction from a physiological vessel comprising:
   a) inserting a catheter into a lumen of the vessel, wherein the catheter comprises:
      i) a proximal end configured to connect to an electrical power supply,
      ii) a distal end connected to a proximal end of an open, tubular catheter head having a proximal end and a distal end and configured to be placed within the lumen of a physiological vessel,
      iii) a first lumen having a proximal opening configured to remain outside of the subject and a distal opening in the distal end of the catheter and facing the proximal end of the open tubular catheter head,
      iv) a gap separating the distal end of the catheter and the proximal end of the catheter head, said gap being configured to allow fluid in the physiological vessel to enter the proximal end of the open tubular catheter head and the distal opening of the first lumen,
      v) at least one structural member connecting the distal end of the catheter and to the proximal end of the open tubular catheter head, and vi) at least one electrically insulated, elongated piezoelectric transducer that spans the gap between the distal end of the catheter and the proximal end of the open tubular catheter head such that a proximal end of the transducer is located inside the distal end of the catheter and a distal end of the transducer is located outside the catheter and either in said gap or in the catheter head;

b) placing the catheter head in the physiological vessel in the immediate vicinity of the obstruction;

c) electrically activating the piezo transducer to produce acoustic streaming in which liquid within the lumen of the vessel flows into the gap between the catheter and the catheter head and through the open, tubular catheter head from the proximal end to the distal end of the catheter head; and d) using the liquid flow generated by the acoustic streaming to disrupt the obstruction.

12. The method of claim 11 wherein:
 a) the catheter further comprises a second lumen containing leads configured to activate the piezo transducer and
 b) fragments resulting from the disruption of the obstruction are removed from the physiological vessel through the first catheter lumen.

13. The method of claim 12 wherein the physiological vessel is a blood vessel, the obstruction is a thrombus, and further comprising the step of delivering a thrombolytic agent through the first catheter lumen to the site of the thrombus.

14. The method of claim 11 wherein the distal end of the at least one elongated piezo transducer is located within 0.4 mm of the proximal end of the catheter head.

15. The method of claim 11 wherein the inner diameter of the physiological vessel is between 2 mm and 10 mm.

16. The method of claim 11 wherein the outer diameter of the catheter head is between 1 mm and 5 mm.

* * * * *